United States Patent [19]

Dornheim et al.

[11] Patent Number: 4,613,982
[45] Date of Patent: Sep. 23, 1986

[54] RADIODIAGNOSTIC APPARATUS FOR MAMMOGRAMS

[75] Inventors: Hans-Peter Dornheim, Bubenreuth; Edmund Saffer, Eggolsheim, both of Fed. Rep. of Germany

[73] Assignee: Siemens Aktiengesellschaft, Berlin and Munich, Fed. Rep. of Germany

[21] Appl. No.: 612,527

[22] Filed: May 21, 1984

[30] Foreign Application Priority Data

May 30, 1983 [DE] Fed. Rep. of Germany ....... 3319622

[51] Int. Cl.$^4$ .......................... A61B 6/04; G03B 42/02
[52] U.S. Cl. ........................................ 378/37; 378/173
[58] Field of Search ................ 378/37, 167, 177, 172, 378/173, 180, 181, 179

[56] References Cited

U.S. PATENT DOCUMENTS 1,722,573  7/1929  Hirsch ................................ 378/172

OTHER PUBLICATIONS

Siemens-Prospekt Nr.M-R 87/1612, "Mammomat B der moderne Mammographie-Arbeitsplatz".
Siemens-Prospekt Nr.M-R 87/1594, "Alle aktuellen Aufnahmetechniken mit dem Mammomat".

Primary Examiner—Craig E. Church
Assistant Examiner—Charles F. Wieland
Attorney, Agent, or Firm—Mark H. Jay

[57] ABSTRACT

The invention relates to a radiodiagnostics apparatus for mammograms with an adjustable x-ray tube fastened to a mount, a compression device, and two recording stages to be selectively aligned with the x-ray tube. The recording stages are pivotably connected with the mount in such a way that one can be brought into a recording position and the second into a parked position.

4 Claims, 3 Drawing Figures

4,613,982

RADIODIAGNOSTIC APPARATUS FOR MAMMOGRAMS

BACKGROUND OF THE INVENTION

The invention relates to a radiodiagnostics apparatus for mammograms having an adjustable x-ray tube attached to a mount, a compression device, and several recording stages selectively alignable with the x-ray tube.

A radiodiagnostics apparatus of this kind is known wherein several different recording stages, in particular of different sizes, are provided, which can be selectively attached to the x-ray tube. To make a mammogram, the physician accordingly selects the desired stage, attaches it to the x-ray tube, and then takes the picture. Attaching the desired stage to the x-ray tube is relatively time-consuming. Also it is necessary to store the stages not used separately from the radiodiagnostics apparatus.

SUMMARY OF THE INVENTION

It is an object of the invention to provide a radiodiagnostics apparatus in which separate storing of the different recording stages is not necessary and where the desired recording stage can easily be brought into the recording position.

According to the invention, this object is achieved in that two recording stages are pivotably connected with the mount in such a way that one can be brought into a recording position and the second into a parked position. The radiodiagnostics apparatus according to the invention carries the two recording stages provided for x-ray pictures, which by simple pivoting can be brought into the respective desired position.

An embodiment of the invention includes two recording stages which are mounted underneath the compression device to swivel about an axis parallel to the central ray of the x-ray source, in such a way that they are opposite each other at 180°. In this embodiment, the desired stage can be brought into the respective recording or parked position by pivoting on the axle connected with the x-ray tube. Another embodiment of the invention includes two recording stages which form with a support pivotable about an axis which is perpendicular to the central ray of the x-ray source, a U-shaped recording unit which externally embraces the x-ray source and the compression device and in which the stages are opposite each other. With this embodiment it suffices to pivot the stages about an axis which is perpendicular to the central ray of the x-ray sources and which also carries the x-ray source, in order to bring the stages into their respective position. To take into account the desire of physicians to make x-ray pictures selectively with or without a scattered-ray grid, the stages may be designed so that the scattered-ray grid provided there can be brought into a position in which it is outside the roentgen radiation.

Other features and advantages of the present invention will become apparent from the following detailed description, and from the claims.

For a full understanding of the present invention, reference should now be made to the following detailed description and to the accompanying drawings.

DETAILED DESCRIPTION

Figure 1:
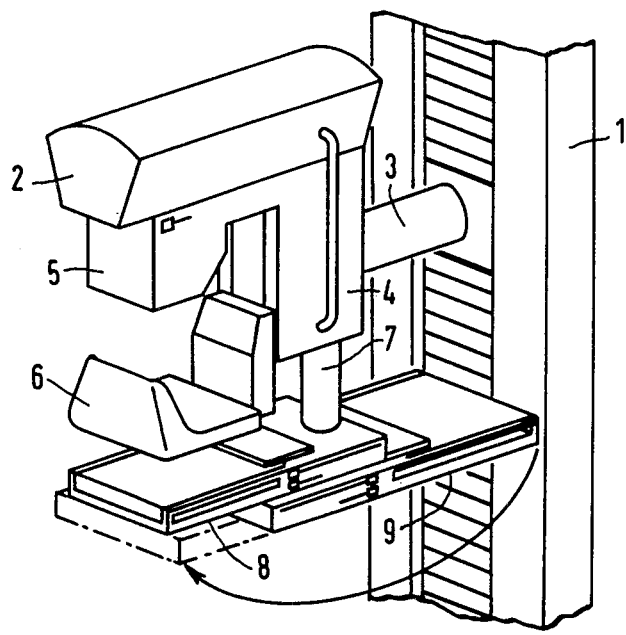
FIGS. 1 and 2 show two embodiments of radiodiagnostics apparatus according to the invention.

In FIG. 1., a stand 1, with which, by means of an axle 3 perpendicular to its central ray, an x-ray source 2 is adjustable in height. Axle 3 carries x-ray source 2 with the aid of block 4 on which is arranged primary radiation barrier 5. Additionally, block 4 carries compression plate 6 which is adjustable by a motor in the direction of the central ray of x-ray source 2.

Fastened parallel to the central ray of x-ray source 2 on block 4 is an axle 7, about which two recording stages 8 and 9 for different cassette sizes are pivotably mounted. In FIG. 1, stage 8 is in the recording position, while stage 9 is in the parked position. If stage 9 is to be used for recording, stages 8 and 9 are jointly swiveled about axle 7 in such a way that stage 9 occupies the recording position and stage 8 the parked position.

Figure 2:
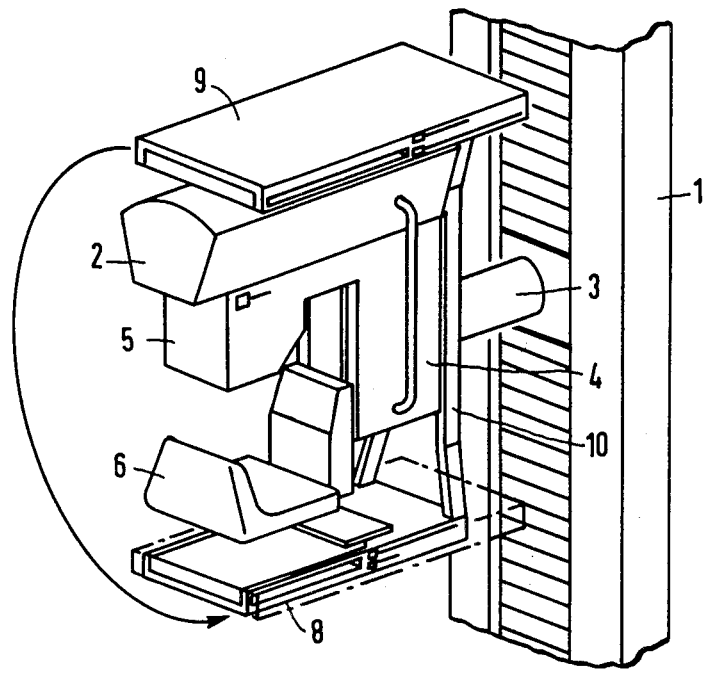

In the embodiment according to FIG. 2, like parts as in the embodiment of FIG. 1 are designed by the same reference symbols. In the embodiment of FIG. 2, two stages 8 and 9, which in the embodiment of FIG. 1 are opposite each other at 180°, form together with support 10 pivotable about axis 3 perpendicular to the central ray of the x-ray source, a U-shaped recording unit. Recording unit 8, 9, 10 embraces x-ray source 2 and compression plate 6 externally, and stages 8 and 9 are opposite each other. In FIG. 2, stage 8 is in the recording position, while stage 9 occupies the parked position above x-ray source 2. If stage 9 is to be moved into the recording position, support 9 is pivoted on axle 3 by 180°, so that it occupies the position of stage 8, and stage 8 the position of stage 9.

Figure 3:
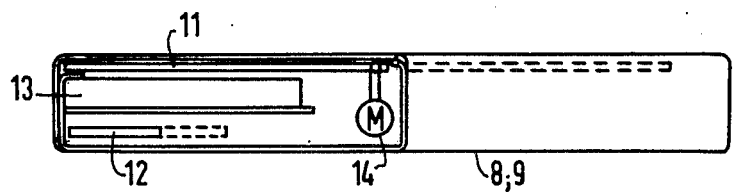
FIG. 3 is a detailed illustration of the radiodiagnostics apparatus according to FIGS. 1 and 2.

Stages 8 and 9 each comprise scattered-ray grid 11 and actinometer chamber 12 of an automatic exposure timer (FIG. 3). The particular x-ray film cassette 13 is inserted between scattered-ray grid 11 and actinometer chamber 12, as shown in FIG. 3. During a take, scattered-ray grid 11 is moved back and forth periodically by means of motor 14, to prevent reproduction on the x-ray film. FIG. 3 shows that stages 8 and 9 are designed so that scattered-ray grid 11 can be brought into a position shown in broken lines in which it lies outside the roentgen radiation, so that x-ray pictures without the scattered-ray grid can be produced. Moving scatter-ray grid 11 into the position shown in broken lines is done appropriately by motor 14, which is suitably controlled for the purpose.

To take the x-ray pictures, the procedure according to FIGS. 1 and 2, is to place the breast on the recording stage which is in the recording position—in the examples this is stage 8—and then to compress it downwardly by adjustment of compression plate 6. Then x-ray tube 2 is turned on, after which compression plate 6 is moved back up, and lastly exposed x-ray film cassette 13 is removed from the respective stage.

There has thus been shown and described a radiodiagnostics apparatus for mammograms which fulfills all the objects and advantages sought therefor. Many changes, modifications, variations and other uses and applications of the subject invention will, however, become apparent to those skilled in the art after considering the specification and the accompanying drawings which disclose embodiments thereof. All such changes, modifications, variations and other uses and applications which do not depart from the spirit and scope of the invention are deemed to be covered by the invention which is limited only by the claims which follow.

What is claimed is:

1. In a mammographic radiodiagnostic apparatus of the type having an x-ray source attached to a mount, a compression device and a plurality of recording stages which are selectively alignable with the x-ray source and are each constructed to receive an individual film cassette, the improvement wherein said plurality of recording stages are pivotally connected to the mount in such a manner that any one of said plurality is alignable with the x-ray source to expose its film cassette, and all others in said plurality are thereupon disaligned with the x-ray source in a non-exposable position.

2. The improvement of claim 1, wherein there are exactly two recording stages which are rotatable about an axis parallel to the central ray from the x-ray source and said stages are diametrically opposed to each other across said axis.

3. The improvement of claim 1, wherein there are exactly two recording stages mounted to opposite ends of a support to form a U-shaped recording unit, said support being rotatable about an axis perpendicular to the central ray of the x-ray source, and said recording unit externally embracing the x-ray source and the compression device.

4. The improvement of claim 1, wherein each recording stage includes a scattered-ray grid which is movable into and out of a beam of x-rays produced by the x-ray source.

* * * * *